United States Patent
Hung

(10) Patent No.: US 10,105,194 B2
(45) Date of Patent: Oct. 23, 2018

(54) ORTHOGNATHIC CORRECTION DEVICE AND ORTHOGNATHIC CORRECTION METHOD

(71) Applicant: Cheng-Hsiang Hung, New Taipei (TW)

(72) Inventor: Cheng-Hsiang Hung, New Taipei (TW)

(*) Notice: Subject to any disclaimer, the term of this patent is extended or adjusted under 35 U.S.C. 154(b) by 135 days.

(21) Appl. No.: 15/080,895

(22) Filed: Mar. 25, 2016

(65) Prior Publication Data

US 2016/0278884 A1    Sep. 29, 2016

(30) Foreign Application Priority Data

Mar. 26, 2015  (CN) .......................... 2015 1 0135110
Mar. 21, 2016  (CN) .......................... 2016 1 0159772

(51) Int. Cl.
*A61C 3/00*   (2006.01)
*A61C 7/36*   (2006.01)
*A61C 7/08*   (2006.01)

(52) U.S. Cl.
CPC .  *A61C 7/36* (2013.01); *A61C 7/08* (2013.01)

(58) Field of Classification Search
CPC .................................... A61C 7/36; A61C 7/08
See application file for complete search history.

(56) References Cited

U.S. PATENT DOCUMENTS

| 5,683,244 A | 11/1997 | Truax |
| 5,711,667 A | 1/1998 | Vogt |
| 5,975,893 A | 11/1999 | Chishti et al. |
| 2003/0190576 A1 | 10/2003 | Phan et al. |
| 2006/0019213 A1 | 1/2006 | Graham et al. |
| 2010/0307511 A1 | 12/2010 | Meade |
| 2012/0295211 A1 | 11/2012 | Frantz et al. |

FOREIGN PATENT DOCUMENTS

| CN | 101636122 A | 1/2010 |
| EP | 2745799 A2 | 6/2014 |
| JP | 2013-523272 | 6/2013 |
| JP | 2014-521481 | 8/2014 |
| WO | WO 2014/016495 A1 | 1/2014 |

OTHER PUBLICATIONS

Europe Patent Office, Search Report, Patent Application Serial No. 16162310.3, dated Jan. 23, 2017, Europe.
Japan Patent Office, Office Action, Patent Application Serial No. 2016-061521, dated Mar. 27, 2017, Japan.
European Patent Office, Partial Search Report, Patent Application Serial No. 16162310.3, dated Sep. 12, 2016.

*Primary Examiner* — Nicholas Lucchesi

(57) ABSTRACT

An orthognathic correction device includes a first retainer, a second retainer and at least two elastic members. The first retainer is configured to be removably worn on the maxillary dental arch of a patient and has at least two first connection parts fixed on the left and right buccal surfaces of the first retainer. The second retainer is configured to be removably worn on the mandibular dental arch of the patient and has at least two second connection parts fixed on the left and right buccal surfaces of the second retainer. The elastic members couple the first and second retainers worn and retained on the maxillary and mandibular dental arches of the patient, respectively, so as to drive the second retainer to move relative to the first retainer, thereby adjusting the relative position between the mandible and the maxilla of the patient.

14 Claims, 6 Drawing Sheets

ORTHOGNATHIC CORRECTION DEVICE AND ORTHOGNATHIC CORRECTION METHOD

CROSS REFERENCE TO RELATED APPLICATIONS

The present application claims priorities of China Patent Application No. 201510135110.3, filed on Mar. 26, 2015, the entirety of which is incorporated by reference herein, and China Patent Application No. 201610159772.9, filed on Mar. 21, 2016.

BACKGROUND OF THE INVENTION

Field of the Invention

The present application relates to an orthognathic correction technology, and in particular to an orthognathic correction device and an orthognathic correction method.

Description of the Related Art

In general, a patient will require orthognathic correction if his temporomandibular joint (TMJ) between the maxilla and the mandible is not in the optimum position, causing an abnormal relative position between the maxilla and the mandible.

Currently, doctors often do an osteotomy to cut the patient's maxilla, mandible, or both, and then to reconstruct the broken bones in the needed positions, so as to achieve orthognathic correction. However, many patients fear the intrusive nature and risks associated with this surgical method and are often hesitant to choose this option.

BRIEF SUMMARY OF THE INVENTION

In view of the aforementioned problems, an object of the invention is to provide an orthognathic correction device, and in particular, to provide a patient removable orthognathic correction device that can be used to achieve orthognathic correction without the surgical method feared by many patients.

An embodiment of the invention provides an orthognathic correction device, including a first retainer, a second retainer and at least two elastic members. The first retainer is configured to be removably worn on the maxillary dental arch of a patient, and has a first left buccal surface with at least one first left connection part fixed thereon and a first right buccal surface with at least one first right connection part fixed thereon. The second retainer is configured to be removably worn on the mandibular dental arch of the patient, and has a second left buccal surface with at least one second left connection part fixed thereon and a second right buccal surface with at least one second right connection part fixed thereon. At least one elastic member is configured to couple the first left connection part to the second left connection part, and at least one elastic member is configured to couple the first right connection part to the second right connection part, such that the elastic members drive the second retainer to move relative to the first retainer, thereby adjusting the relative position between the mandible and the maxilla of the patient when the first retainer and second retainer are retained on the maxillary and mandibular dental arches, respectively.

Another embodiment also provides an orthognathic correction method, including: coupling a first retainer with a maxillary dental arch of a patient, wherein the first retainer is configured to be removably worn on the maxillary dental arch, and the first retainer has a first left buccal surface with at least one first left connection part fixed thereon and a first right buccal surface with at least one first right connection part fixed thereon; coupling a second retainer with a mandibular dental arch of the patient, wherein the second retainer is configured to be removably worn on the mandibular dental arch, and the second retainer has a second left buccal surface with at least one second left connection part fixed thereon and a second right buccal surface with at least one second right connection part fixed thereon; and coupling at least one elastic member to the first left connection part and to the second left connection part, and coupling at least one elastic member to the first right connection part and to the second right connection part, so as to drive the second retainer to move relative to the first retainer, thereby adjusting a relative position between a mandible and a maxilla of the patient.

Another embodiment also provides an orthognathic correction method, including: coupling a first retainer with a maxillary dental arch of a patient, wherein the first retainer is configured to be removably worn on the maxillary dental arch, and the first retainer has a first left buccal surface with at least one first left connection part fixed thereon and a first right buccal surface with at least one first right connection part fixed thereon; providing at least one second left connection part fixed on a left buccal surface of a mandibular dental arch of the patient, and providing at least one second right connection part fixed on a right buccal surface of the mandibular dental arch; and coupling at least one elastic member to the first left connection and to the second left connection part, and coupling at least one elastic member to the first right connection part and to the second right connection part, so as to drive the mandibular dental arch to move relative to the first retainer, thereby adjusting a relative position between a mandible and a maxilla of the patient.

Another embodiment also provides an orthognathic correction method, including: coupling a second retainer with a mandibular dental arch of a patient, wherein the second retainer is configured to be removably worn on the mandibular dental arch, and the second retainer has a second left buccal surface with at least one second left connection part fixed thereon and a second right buccal surface with at least one second right connection part fixed thereon; providing at least one first left connection part fixed on a left buccal surface of a maxillary dental arch of the patient, and providing at least one first right connection part fixed on a right buccal surface of the maxillary dental arch; and coupling at least one elastic member to the second left connection part and to the first left connection part, and coupling at least one elastic member to the second right connection part and to the first right connection part, so as to drive the second retainer to move relative to the maxillary dental arch, thereby adjusting a relative position between a mandible and a maxilla of the patient.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1A:
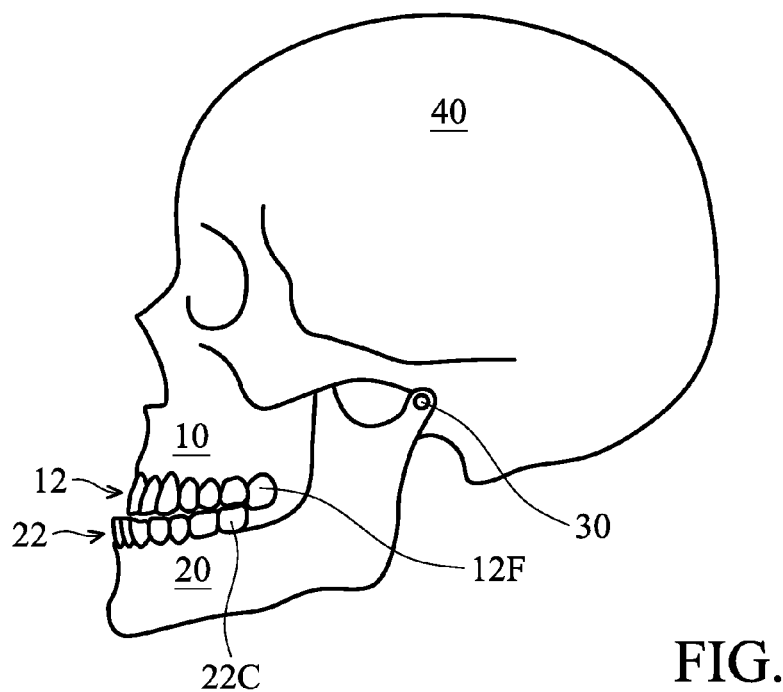
FIGS. 1A and 1B are schematic views illustrating the relative relationship of a patient's skull, maxilla and mandible in common cases.

In order to illustrate the purposes, features, and advantages of the invention, the preferred embodiments and drawings of the invention are shown in detail as follows.

In the following detailed description, the orientations of "on", "above", "under", "below", "left" and "right" are used for representing the relationship between the relative positions of each element as illustrated in the drawings, and are not meant to limit the invention. Also, the relationship between the relative positions of each element can be referred to the orthogonal coordinates including an X-axis, a Y-axis, and a Z-axis as shown in the drawings. In addition, the present disclosure may repeat reference numerals and/or letters in the various examples for the purpose of simplicity and clarity.

Figure 1B:
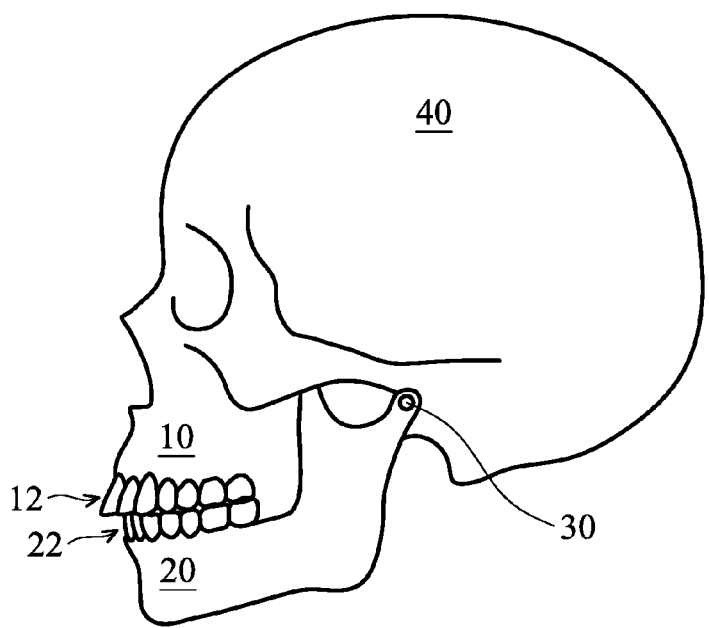

FIGS. 1A and 1B are schematic views illustrating the relative relationship of a patient's skull 40, maxilla 10 and mandible 20 in common cases, wherein the maxilla 10 is fixedly connected to the skull 40 and the mandible 20 is movably connected to the skull 40 via the temporomandibular joint 30. Also, the patient's maxillary dental arch 12 and mandibular dental arch 22 are connected to the maxilla 10 and the mandible 20, respectively. When the patient's temporomandibular joint 30 between the maxilla 10 and the mandible 20 is not in the optimum position, it may cause the mandible 20 with respect to the maxilla 10 to be prognathic (FIG. 1A) or retracted (FIG. 1B), so that a malocclusion of the maxillary and mandibular dental arches 12 and 22 will happen. Consequently, the appearance of the patient's teeth, oral functions such as chewing, pronunciation, and oral health concerns such as dental cavities and wear of teeth, may also be adversely affected.

As described above, an object of the invention is to provide an orthognathic correction device, and in particular to provide a patient removable orthognathic correction device that can be used to achieve orthognathic correction without the surgical method feared by patients.

Figure 2:
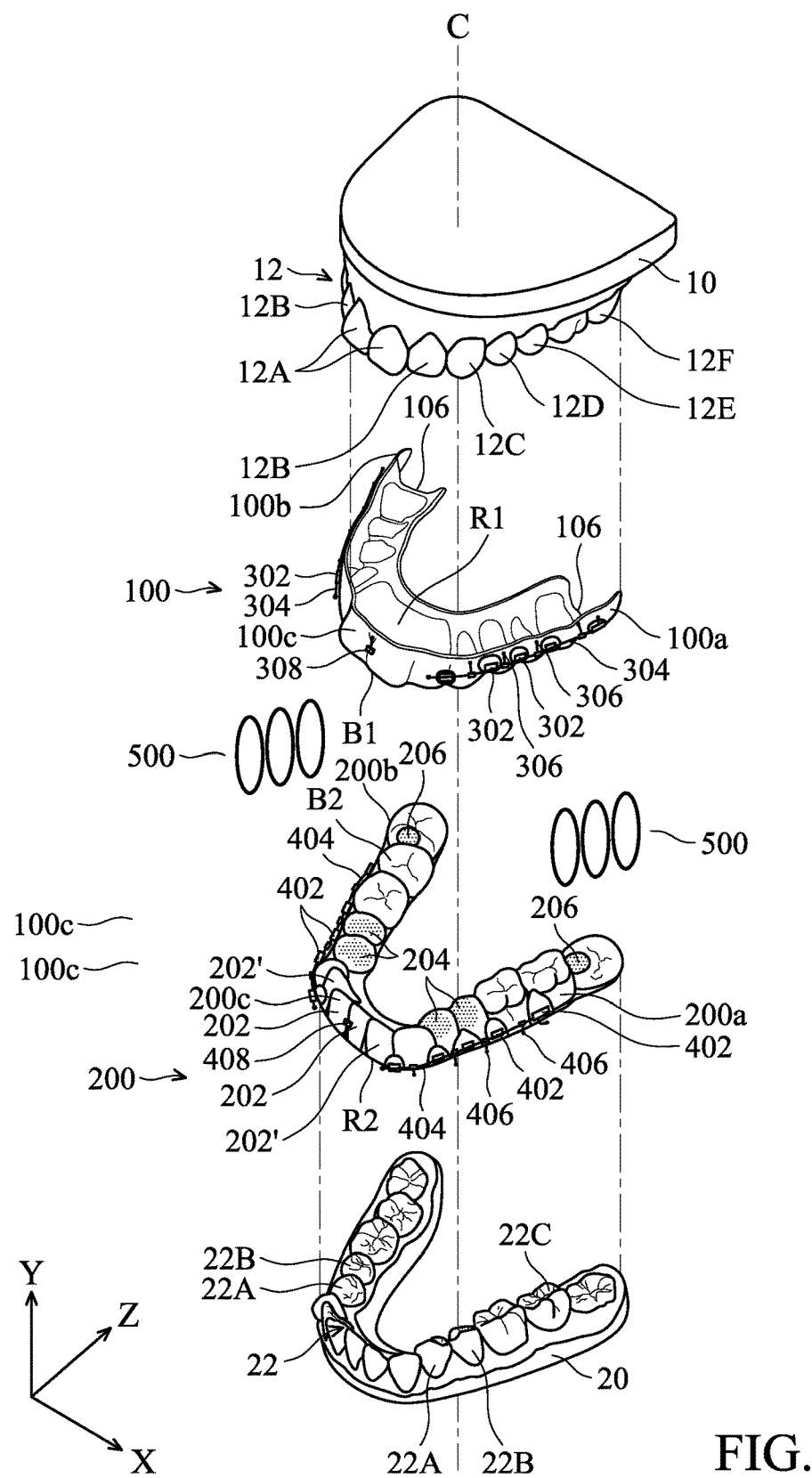
FIG. 2 is a schematic view illustrating the relative relationship of an orthognathic correction device and a patient's maxillary dental arch and mandibular dental arch according to an embodiment of the invention.

FIG. 2 is a schematic view illustrating the relative relationship of an orthognathic correction device and a patient's maxillary dental arch 12 and mandibular dental arch 22 according to an embodiment of the invention. As shown in FIG. 2, the orthognathic correction device primarily includes a first retainer 100, a second retainer 200, and several elastic members 500. Moreover, there are several first brackets 302, first arch wires 304, and first connection parts 306 disposed on the first retainer 100, and there are several second brackets 402, second arch wires 404, and second connection parts 406 disposed on the second retainer 200.

The first retainer 100 has a first teeth receiving part R1 and a first occlusal face B1 opposite to each other. Also, the second retainer 200 has a second teeth receiving part R2 and a second occlusal face B2 opposite to each other. The first occlusal face B1 corresponds to the second occlusal face B2. The first and second teeth receiving parts R1 and R2 form receiving spaces for accommodating the maxillary and mandibular dental arches 12 and 22, respectively.

It should be appreciated that the first retainer 100 and the second retainer 200 are removable retainers (also known as movable retainers), so that the patient can freely wear or remove the retainers depending on situations and according to demand, and can still brush his teeth normally. In some embodiments, the first retainer 100 and the second retainer 200 may comprise thermoplastic, synthetic resin or other materials suitable for use in oral applications.

As shown in the embodiment of FIG. 2, the first retainer 100 further has a first left buccal surface 100a and a first right buccal surface 100b opposite to each other. The first brackets 302 are mounted on the first left buccal surface 100a and the first right buccal surface 100b (e.g. the first left buccal surface 100a and the first right buccal surface 100b each have five first brackets 302 thereon). The first arch wires 304 (e.g. two first arch wires 304) respectively pass through the first brackets 302 on the first left buccal surface 100a and the first right buccal surface 100b and are fixed by the first brackets 302. Moreover, the first arch wires 304 each has first connection parts 306 (e.g. four first connection parts 306, each having a hook structure) attached, and the first connection parts 306 are located between the first brackets 302.

Similarly, the second retainer 200 further has a second left buccal surface 200a and a second right buccal surface 200b opposite to each other, wherein the second left buccal surface 200a corresponds to the first left buccal surface 100a of the first retainer 100 and the second right buccal surface 200b corresponds to the first right buccal surface 100b of the first retainer 100. The second brackets 402 are mounted on the second left buccal surface 200a and the second right buccal surface 200b (e.g. the second left buccal surface 200a and the second right buccal surface 200b each have five second brackets 402 thereon). The second arch wires 404 (e.g. two second arch wires 404) respectively pass through the second brackets 402 on the second left buccal surface 200a and the second right buccal surface 200b and are fixed by the second brackets 402. Moreover, the second arch wires 404 each has second connection parts 406 (e.g. four second connection parts 406, each having a hook structure) attached, and the second connection parts 406 are located between the second brackets 402.

In some embodiments, the first and second brackets 302 and 402 may comprise stainless steel, Ni—Ti alloy or plastic ceramic materials. The first and second arch wires 304 and 404 as well as the first and second connection parts 306 and 406 may comprise stainless steel or Ni—Ti alloy material.

As shown in FIG. 2, the elastic members 500 are used to couple the first connection parts 306 (i.e. the first left connection parts) on the first left buccal surface 100a to the second connection parts 406 (i.e. the second left connection parts) on the second left buccal surface 200a and are used to couple the first connection parts 306 (i.e. the first right connection parts) on the first right buccal surface 100b to the second connection parts 406 (i.e. the second right connection parts) on the second right buccal surface 200b (e.g. the left buccal surface and the right buccal surface of the first and second retainers 100 and 200 are respectively arranged with three elastic members 500), so that the elastic force of the elastic members 500 can drive the second retainer 200 to move backward and upward (along a direction between the Y-axis and the Z-axis) or move forward and downward (along a direction between the -Y-axis and the -Z-axis) relative to the first retainer 100. Accordingly, the relative position between the patient's mandible 20 connected to the second retainer 200 and the patient's maxilla 10 connected to the first retainer 100 can be adjusted, thereby achieving orthognathic correction.

It should be noted that when the method of the elastic members 500 coupling the first and second connection parts 306 and 406 on the corresponding buccal surfaces of the first retainer 100 and the second retainer 200 changes, it may generate an elastic force for driving the second retainer 200 to move backward and upward (along a direction between the Y-axis and the Z-axis) or move forward and downward (along a direction between the -Y-axis and the -Z-axis) relative to the first retainer 100. In some embodiments, the elastic members 500 may be annuluses, such as rubber bands or spring coils made of Ni—Ti alloy material, having the same or different elastic force.

Specifically, when the numbers and elastic force of the elastic members 500 arranged on the left and right buccal surfaces of the first retainer 100 and the second retainer 200 match each other, it may make the left and right buccal surfaces of the first retainer 100 and the second retainer 200 bear uniform force, thus preventing the mandible 20 connected to the second retainer 200 from rotating with respect to the maxilla 10 connected to the first retainer 100 along a virtual central axis C (parallel to the Y-axis in FIG. 2) of the patient's mouth, and resulting in the relative movement between the mandible 20 and the maxilla 10 being only along the direction between the Y-axis and the Z-axis or the direction between the -Y-axis and the -Z-axis in FIG. 2. However, in some embodiments, the numbers and elastic force of the elastic members 500 arranged on the left and right buccal surfaces of the first retainer 100 and the second retainer 200 may not match, accommodating different conditions of different patients.

Moreover, the locations and numbers of the first and second brackets 302 and 402, the numbers and lengths of the first and second arch wires 304 and 404, the locations and numbers of the first and second (left and right) connection parts 306 and 406, and the numbers of the elastic members 500 are not limited to the embodiment of FIG. 2, but can be adjusted according to requirements.

Still referring to FIG. 2, the orthognathic correction device may further include a first central connection part 308 (e.g. a hook structure) fixedly mounted on the labial surface 100c between the first left buccal surface 100a and the first right buccal surface 100b of the first retainer 100. Also, at least one elastic member 500 can be used to couple the first central connection part 308 and a first connection part 306 on the first left buccal surface 100a or the first right buccal surface 100b, and then to couple the first connection part 306 and the corresponding second connection part 406 (with a position posterior to the first connection part 306) on the second retainer 200, so that the elastic force of the elastic member 500 can drive the second retainer 200 to move relative to the first retainer 100 along the X-direction or the -X-direction as shown in FIG. 2, thereby correcting horizontal asymmetry between the maxilla 10 and the mandible 20. Similarly, as shown in FIG. 2, the orthognathic correction device may further include a second central connection part 408 (e.g. a hook structure) fixedly mounted on the labial surface 200c between the second left buccal surface 200a and the second right buccal surface 200b of the second retainer 200. Also, at least one elastic member 500 can be used to couple the second central connection part 408 and a second connection part 406 on the second left buccal surface 200a or the second right buccal surface 200b, and then to connect the second connection part 406 and the corresponding first connection part 306 (with a position posterior to the second connection part 406) on the first retainer 100, thereby correcting horizontal asymmetry of the maxilla 10 and the mandible 20.

In some embodiments, the material and assembly methods of the first and second central connection parts 308 and 408 are the same as the first and second connection parts 306 and 406.

Figure 3A:
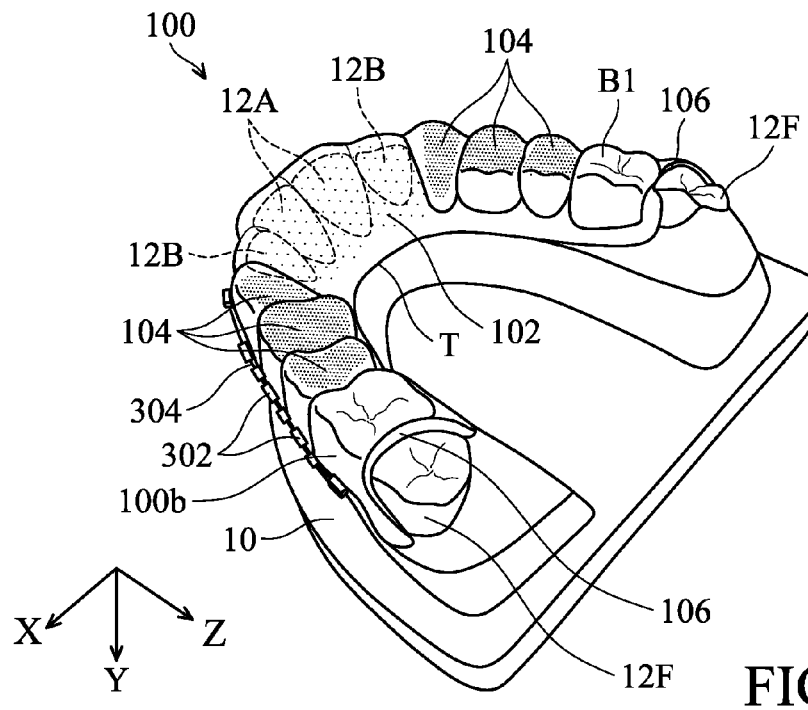
FIG. 3A is a schematic view illustrating a first retainer according to an embodiment of the invention being worn on a patient's maxillary dental arch.
Figure 3B:
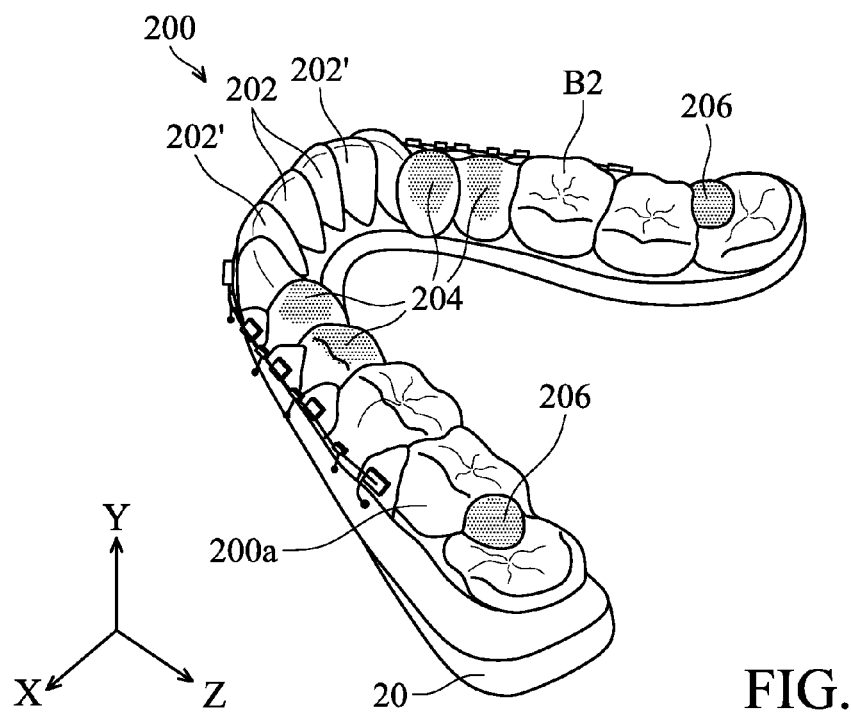
FIG. 3B is a schematic view illustrating a second retainer according to an embodiment of the invention being worn on a patient's mandibular dental arch.

FIG. 3A is a schematic view illustrating a first retainer 100 according to an embodiment of the invention being worn on a patient's maxillary dental arch. FIG. 3B is a schematic view illustrating a second retainer 200 according to an embodiment of the invention being worn on a patient's mandibular dental arch.

As shown in FIGS. 3A and 3B, it should be appreciated that when the first retainer 100 and second retainer 200 are worn on the maxillary and mandibular dental arches, they are substantially covering the entire crown of the maxillary and mandibular dental arches. More specifically, the first retainer 100 and the second retainer 200 are designed according to the undercut structure of the maxillary and mandibular dental arches, so that the first retainer 100 and the second retainer 200 can conformably cover the entire crown of the maxillary and mandibular dental arches, thus strengthening the retention of the first and second retainer 100 and 200 engaging with the maxillary and mandibular dental arches. Thus, it can prevent the first retainer 100 and the second retainer 200 from easily separating from the maxillary and mandibular dental arches during orthognathic correction.

Referring to FIG. 3A, a thickened part 102 and several thickened parts 104 are formed on the first occlusal face B1 of the first retainer 100. Specifically, the position of the thickened part 102 corresponds to two incisors 12A and two lateral incisors 12B of the maxillary dental arch (see FIG. 2), and the positions of the thickened parts 104 correspond to the (left and right) canines 12C, first premolars 12D and second premolars 12E, respectively, of the maxillary dental arch (see FIG. 2). Furthermore, the thickened part 102 forms a guiding surface which starts from the top of the incisors 12A and 12B and gradually descends toward a palatal side T, and the thickened parts 104 also form guiding surfaces which start from the thickest parts of the thickened parts 104 (corresponding to the centers of the canines 12C, the first premolars 12D and the second premolars 12E) and gradually descend toward the thinnest parts of the thickened parts 104 (located in adjacent places of the aforementioned teeth). The guiding surfaces of the thickened part 102 and the thickened parts 104 may be flat or curved.

Similarly, referring to FIG. 3B, several thickened parts 204 are formed on the second occlusal face B2 of the second retainer 200. Specifically, the positions of the thickened parts 204 correspond to the (left and right) first premolars 22A and second premolars 22B, respectively, of the mandibular dental arch (see FIG. 2). The thickest parts of the thickened parts 204 correspond to the centers of the first premolars 22A and the second premolars 22B.

Note that the term "thickened part" used in the present disclosure represents, for example, that the regions of the first occlusal face B1 corresponding to the thickened parts 102 and 104 each have a greater thickness than the other regions of the first occlusal face B1 (having no thickened part), and the regions of the second occlusal face B2 corresponding to the thickened parts 204 each have a greater thickness that the other regions of the second occlusal face B2 (having no thickened part).

In some embodiments, the first retainer 100 and the thickened parts 102 and 104 may be integrally formed in one piece. Alternatively, the thickened parts 102 and 104 may be formed of synthetic resin, glass ionomer or other wear-resistant materials suitable for use in oral applications, and then be bonded to the first occlusal face B1 of the first retainer 100. Similarly, the second retainer 200 and the thickened parts 204 may be integrally formed in one piece. Alternatively, the thickened parts 204 may be formed of synthetic resin, glass ionomer or other wear-resistant materials suitable for use in oral applications, and then be bonded to the second occlusal face B2 of the second retainer 200.

When the patient wears the orthognathic correction device as described above, and the first occlusal face B1 of the first retainer 100 contacts the second occlusal face B2 of the second retainer 200, several subunits 202 and 202' (FIGS. 2 and 3B) of the second retainer 200 corresponding to two incisors and two lateral incisors of the mandibular dental arch may contact the thickened part 102 (FIG. 3A) on the first retainer 100, and the thickened parts 204 (FIG. 3B) on the second retainer 200 may contact the thickened parts 104 (FIG. 3A) on the first retainer 100.

Figure 4:
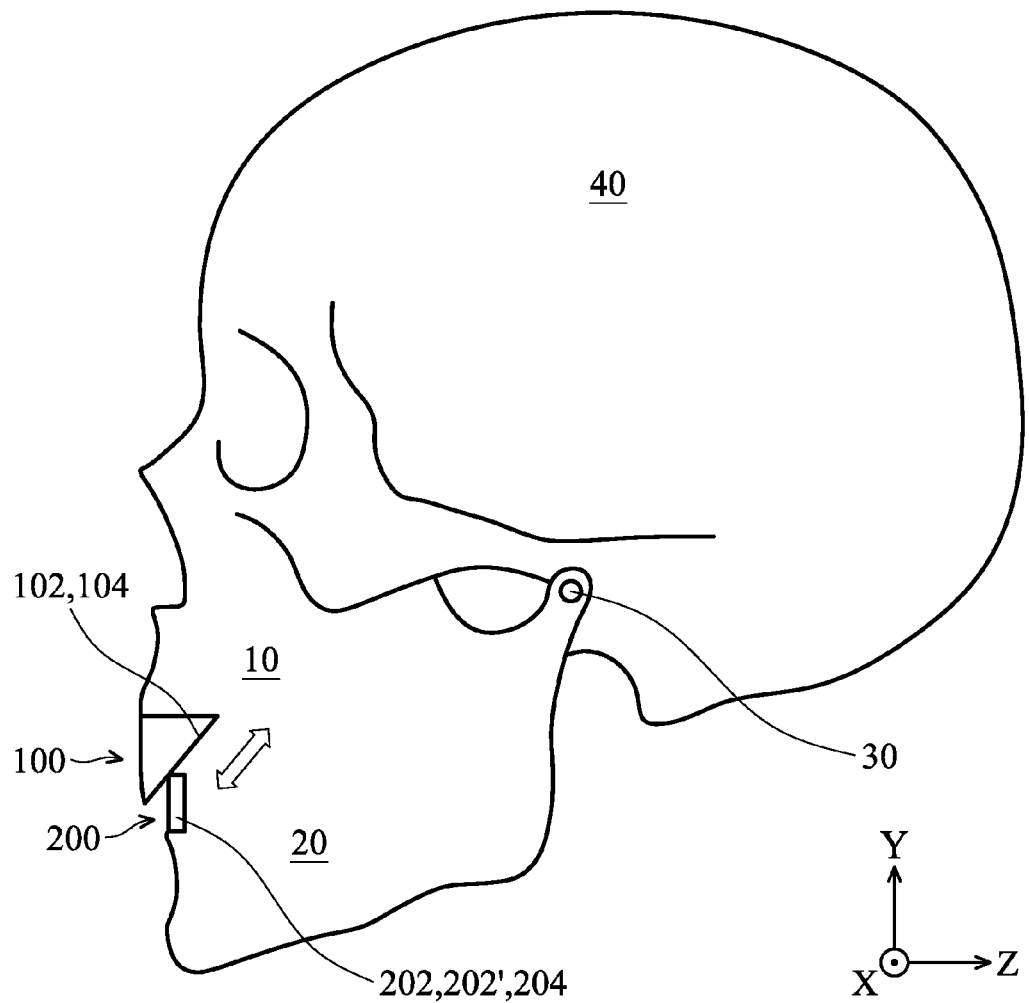
FIG. 4 is a schematic view illustrating the working principle of an orthognathic correction device according to an embodiment of the invention.

FIG. 4 is a schematic view illustrating the working principle of an orthognathic correction device according to an embodiment of the invention. With the above structural design, when the first occlusal face B1 of the first retainer 100 contacts the second occlusal face B2 of the second retainer 200, the thickened parts 102 and 104 on the first occlusal face B1 can be used as guiding blocks, and the subunits 202, 202' and the thickened parts 204 on the second occlusal face B2 can contact the guiding surfaces of the guiding blocks 102 and 104 (in order to simplify the drawing, only one guiding surface and one contact point are depicted in FIG. 4). In this state, the elastic force exerted by the elastic members 500 (FIG. 2) can drive the second retainer 200 to slide along the guiding surfaces relative to the first retainer 100 (as the arrow indicates in FIG. 4), thereby leading the mandible 20 connected to the second retainer 200 to move relative to the maxilla 10 connected to the first retainer 100 and bring the temporomandibular joint 30 back to the appropriate location, so as to achieve t orthognathic correction.

When the elastic force of the elastic members 500 drives the second retainer 200 to move backward and upward (along the direction between the Y-axis and the Z-axis) relative to the first retainer 100, it may improve the case that the patient's mandible 20 is prognathic with respect to the maxilla 10 as shown in FIG. 1A. Conversely, when the elastic force of the elastic members 500 drives the second retainer 200 to move forward and downward (along the direction between the -Y-axis and the -Z-axis) relative to the first retainer 100, it may improve the case that the patient's mandible 20 is retracted with respect to the maxilla 10 as shown in FIG. 1B.

Although the guiding blocks and the guiding surfaces are formed on the first occlusal face B1 of the first retainer 100 in the aforementioned embodiments, they may also be formed on the second occlusal face B2 of the second retainer 200.

The locations and numbers of the thickened parts 102, 104 of the first retainer 100 and the thickened parts 204 of the second retainer 200 are not limited to the embodiments of FIGS. 3A and 3B, but can be adjusted according to the different conditions of different patients.

Furthermore, in cases where the patient's mandible 20 is prognathic with respect to the maxilla 10, the second molar 12F of the maxillary dental arch 12 is often likely to obstruct the second molar 12C of the mandibular dental arch 22 (FIG. 1A), resulting in the second retainer 200 placed on the mandibular dental arch 22 becoming stuck when it is coupled to the first retainer 100 placed on the maxillary dental arch 12, so that the mandible 20 cannot smoothly move backward and upward (along the direction between the Y-axis and the Z-axis) relative to the maxilla 10 during orthognathic correction.

Referring to FIGS. 3A and 3B, it is therefore that the first occlusal face B1 of the first retainer 100 may further have two openings 106 formed thereon for exposing the left and right second molars 12F of the maxillary dental arch 12, and the second occlusal face B2 of the second retainer 200 may further form two spacers 206 thereon corresponding to the openings 106, respectively, of the first retainer 100. It should be noted that, when the first occlusal face B1 of the first retainer 100 contacts the second occlusal face B2 of the second retainer 200, the spacers 206 can abut the second molars 12F through the openings 106, so as to increase the space between the first retainer 100 from the second retainer 200, thus preventing the second retainer 200 from becoming stuck against the first retainer 100. Therefore, the orthognathic device of this embodiment can smoothly adjust the relative position between the mandible 20 connected to the second retainer 200 and the maxilla 10 connected to the first retainer 100, so as to achieve orthognathic correction. It should also be realized that the orthognathic device of this embodiment may further cause a rotation of the mandible 20.

In this embodiment, the spacer 206 can also be regarded as a thickened part, and the manufacturing method thereof is the same as the thickened parts 204. Moreover, in some embodiments, the locations and numbers of the spacers 206 and the openings 106 can also be adjusted. In some embodiments, the openings on the first occlusal face B1 or the second occlusal face B2 can also be omitted.

Although, in the aforementioned embodiments, the orthognathic correction device includes a first retainer 100 and a second retainer 200, the orthognathic correction device in some embodiments may also include a single retainer (a first retainer 100 or a second retainer 200) configured to be removably worn on the maxillary dental arch or the mandibular dental arch. In these cases, there may also be at least two connection parts (i.e. left and right connection parts) fixed on the left buccal surface and the right buccal surface of the other dental arch without a retainer (for example, if the retainer is worn on the maxillary dental arch, at least two connection parts can be fixed on the left and right buccal surfaces of the mandibular dental arch; conversely, if the retainer is worn on the mandibular dental arch, at least two connection parts can be fixed on the left and right buccal surfaces of the maxillary dental arch), and the occlusal face of this dental arch without a retainer may further form thickened parts (guiding blocks) thereon. Therefore, by using elastic members to couple the connection parts on the retainer and the connection parts on the dental arch without a retainer so as to drive the mandible to move relative to the maxilla, the purpose of orthognathic correction can also be achieved. Moreover, the dental arch without a retainer may also have a central connection part on its labial surface between the left and right buccal surfaces, and the central connection part can be coupled to the connection part on the adjacent left or right buccal surface and then be coupled to the connection part on the corresponding left or right buccal surface of the retainer worn on the other dental arch by an elastic member, so as to correct horizontal asymmetry between the maxilla 10 and the mandible 20 as described above.

Although, in the aforementioned embodiments (see FIG. 2), the first teeth receiving part R1 of the first retainer 100 is shaped to encase all (maxillary teeth) of the maxillary dental arch 12 and the second teeth receiving part R2 of the second retainer 200 is shaped to encase all (mandibular teeth) of the mandibular dental arch 22, the first teeth receiving part R1 may also be shaped to encase a part (of maxillary teeth) of the maxillary dental arch 12 and the second teeth receiving part R2 may also be shaped to encase a part (of mandibular teeth) of the mandibular dental arch 22.

Figure 5A:
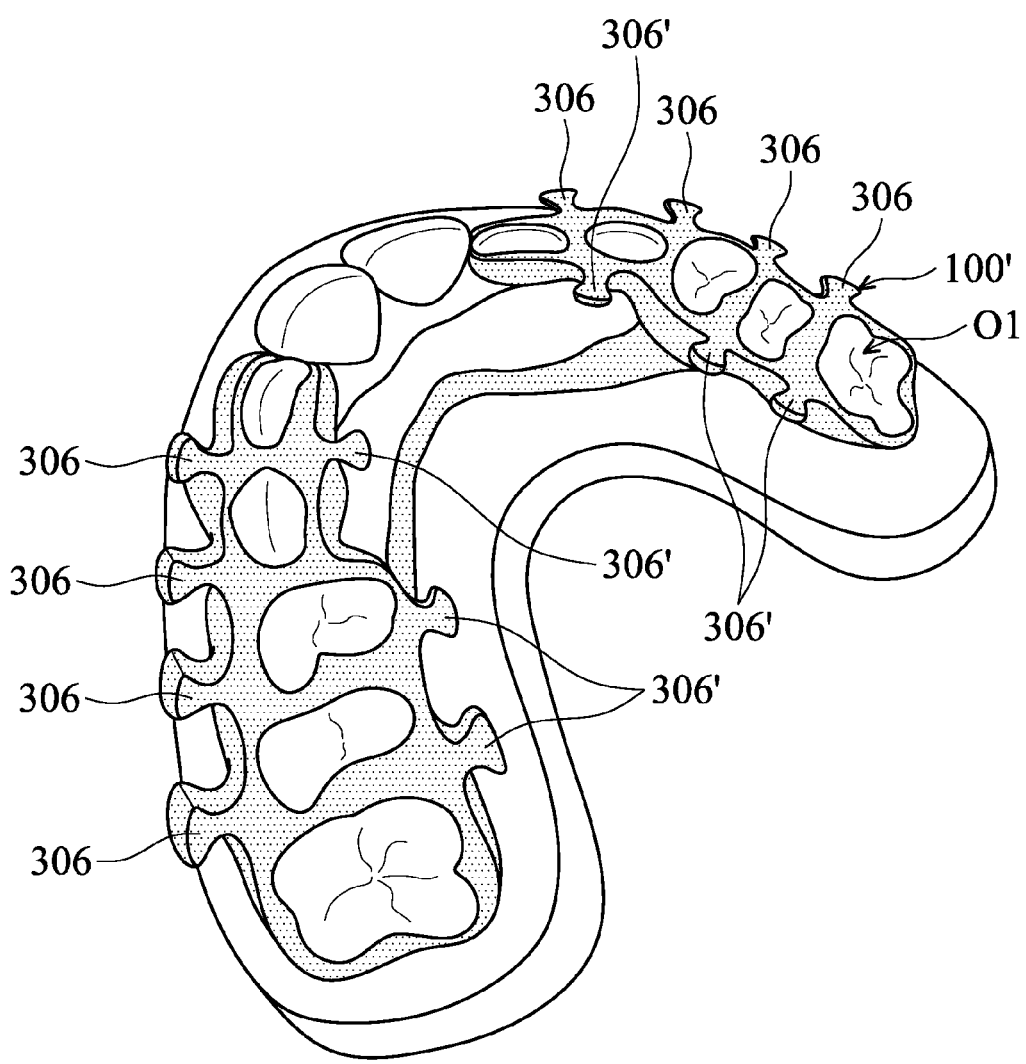
FIG. 5A is a schematic view illustrating a first retainer according to another embodiment of the invention being worn on a patient's maxillary dental arch.
Figure 5B:
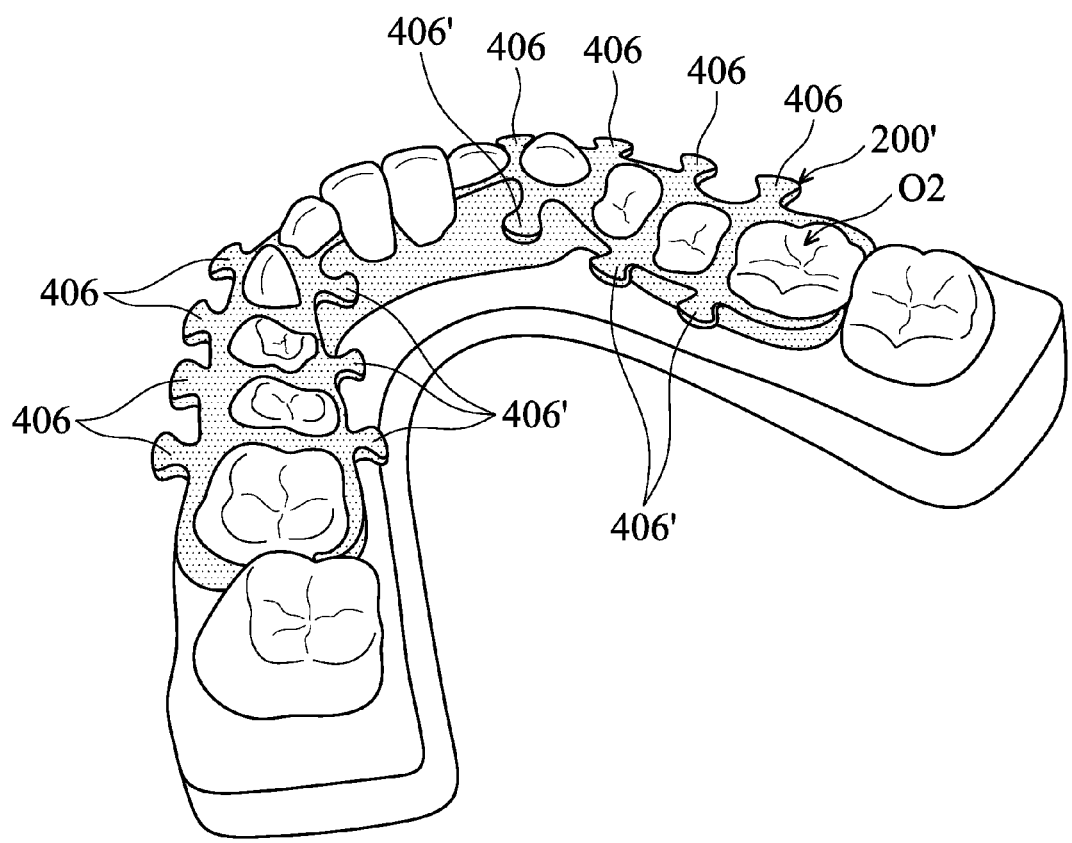
FIG. 5B is a schematic view illustrating a second retainer according to another embodiment of the invention being worn on a patient's mandibular dental arch.

Furthermore, please refer to FIGS. 5A and 5B, wherein FIG. 5A is a schematic view illustrating a first retainer 100' according to another embodiment of the invention being worn on a patient's maxillary dental arch, and FIG. 5B is a schematic view illustrating a second retainer 200' according to another embodiment of the invention being worn on a patient's mandibular dental arch. As shown in FIGS. 5A and 5B, the first retainer 100' may also expose the occlusal surface O1 of the maxillary dental arch 12 instead of covering it almost entirely as in the embodiment of FIG. 3A, and the second retainer 200' may also expose the occlusal surface O2 of the mandibular dental arch 22 instead of covering it almost entirely as in the embodiment of FIG. 3B. It should be realized that, by using several elastic members 500 (see FIG. 2) described above to couple the first connection parts 306 on the buccal surfaces of the first retainer 100' to the second connection parts 406 on the buccal surfaces of the second retainer 200', the orthognathic correction can also be achieved.

As shown in FIGS. 5A and 5B, there may also be at least one first lingual connection part 306' fixed on the lingual surface of the first retainer 100', and there may also be at least one second lingual connection part 406' fixed on the lingual surface of the second retainer 200'. The first and second lingual connection parts 306' and 406' may have the same material as the first and second connection parts 306 and 406 in the embodiment of FIG. 2. In this embodiment (FIGS. 5A and 5B), the first retainer 100', the first connection parts 306, and the first lingual connection parts 306' may be integrally formed (e.g. by metal molding) in one-piece, and the second retainer 200', the second connection parts 406, and the second lingual connection parts 406' may be integrally formed (e.g. by metal molding) in one-piece, but the invention is not limited thereto.

Although embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:

1. An orthognathic correction device, comprising:
    a first retainer configured to be removably worn on a maxillary dental arch of a patient, having a first left buccal surface with at least one first left connection part fixed thereon, and a first right buccal surface with at least one first right connection part fixed thereon;
    a second retainer configured to be removably worn on a mandibular dental arch of the patient, having a second left buccal surface with at least one second left connection part fixed thereon, and a second right buccal surface with at least one second right connection part fixed thereon; and
    at least one elastic member configured to couple the first left connection part to the second left connection part, and at least one elastic member configured to couple the first right connection part to the second right connection part, such that the elastic members drive the second retainer to move relative to the first retainer, thereby adjusting a relative position between a mandible and a maxilla of the patient, when the first retainer and second retainer are retained on the maxillary and mandibular dental arches, respectively;
    wherein the second retainer further has a second occlusal face with at least one spacer formed thereon, and the first retainer further has a first occlusal face with at least one opening formed thereon for exposing at least one maxillary tooth of the maxillary dental arch, and when the first occlusal face contacts the second occlusal face, the spacer abuts the maxillary tooth through the opening to push the maxillary tooth upward.

2. The orthognathic correction device as claimed in claim 1, wherein the second retainer further has a labial surface with a second central connection part fixed thereon, and the orthognathic correction device further comprises at least one elastic member which is configured to couple the second central connection part to the second left connection part and to the first left connection part or which is configured to couple the second central connection part to the second right connection part and to the first right connection part, so as to correct horizontal asymmetry between the mandible and the maxilla of the patient.

3. The orthognathic correction device as claimed in claim 1, wherein the first occlusal face has at least one guiding block formed thereon, and the guiding block has a guiding surface configured to make the second occlusal face contact and move along the guiding surface when the second retainer moves relative to the first retainer.

4. The orthognathic correction device as claimed in claim 1, wherein the first occlusal face has at least one thickened part formed thereon, and the thickened part has a guiding surface configured to make the second occlusal face contact and move along the guiding surface when the second retainer moves relative to the first retainer.

5. The orthognathic correction device as claimed in claim 4, wherein the second occlusal face has at least one corresponding thickened part formed thereon, and the corresponding thickened part on the second occlusal face contacts and moves along the guiding surface of the thickened part on the first occlusal face when the second retainer moves relative to the first retainer.

6. The orthognathic correction device as claimed in claim 1, wherein the first retainer further has a receiving part shaped to encase a part of the maxillary dental arch of the patient.

7. The orthognathic correction device as claimed in claim 1, wherein the second retainer further has a receiving part shaped to encase a part of the mandibular dental arch of the patient.

8. The orthognathic correction device as claimed in claim 1, wherein the first retainer exposes an occlusal surface of the maxillary dental arch of the patient.

9. The orthognathic correction device as claimed in claim 1, wherein the second retainer exposes an occlusal surface of the mandibular dental arch of the patient.

10. The orthognathic correction device as claimed in claim 1, wherein the first retainer further has a lingual surface with at least one first lingual connection part fixed thereon.

11. The orthognathic correction device as claimed in claim 1, wherein the second retainer further has a lingual surface with at least one second lingual connection part fixed thereon.

12. An orthognathic correction method, comprising:
coupling a first retainer with a maxillary dental arch of a patient, wherein the first retainer is configured to be removably worn on the maxillary dental arch, and the first retainer has a first left buccal surface with at least one first left connection part fixed thereon and a first right buccal surface with at least one first right connection part fixed thereon;
coupling a second retainer with a mandibular dental arch of the patient, wherein the second retainer is configured to be removably worn on the mandibular dental arch, and the second retainer has a second left buccal surface with at least one second left connection part fixed thereon and a second right buccal surface with at least one second right connection part fixed thereon;
providing at least one spacer formed on a second occlusal face of the second retainer; and
providing at least one opening formed on a first occlusal face of the first retainer corresponding to the spacer for exposing at least one maxillary tooth of the maxillary dental arch, so that when the first occlusal face contacts the second occlusal face, the spacer abuts the maxillary tooth through the opening to push the maxillary tooth upward; and
coupling at least one elastic member to the first left connection part and to the second left connection part, and coupling at least one elastic member to the first right connection part and to the second right connection part, so as to drive the second retainer to move relative to the first retainer, thereby adjusting a relative position between a mandible and a maxilla of the patient.

13. The orthognathic correction method as claimed in claim 12, further comprising:
providing a second central connection part fixed on a labial surface between the second left and right buccal surfaces of the second retainer; and
coupling at least one elastic member to the second central connection part, to the second left connection part, and to the first left connection part, or coupling at least one elastic member to the second central connection part, to the second right connection part, and to the first right connection part, so as to correct horizontal asymmetry between the mandible and the maxilla of the patient.

14. The orthognathic correction method as claimed in claim 12, further comprising:
providing at least one guiding block formed on the first occlusal face of the first retainer, the guiding block having a guiding surface such that the second occlusal face of the second retainer contacts and moves along the guiding surface when the second retainer moves relative to the first retainer.

* * * * *